(12) United States Patent
Neuman

(10) Patent No.: US 11,519,910 B2
(45) Date of Patent: Dec. 6, 2022

(54) LATERAL FLOW ASSAY DEVICE

(71) Applicant: FibroTx OÜ, Tallinn (EE)

(72) Inventor: Toomas Neuman, Tallinn (EE)

(73) Assignee: FIBROTX OÜ, Tallinn (EE)

(*) Notice: Subject to any disclaimer, the term of this patent is extended or adjusted under 35 U.S.C. 154(b) by 1539 days.

(21) Appl. No.: 14/890,842

(22) PCT Filed: May 12, 2014

(86) PCT No.: PCT/EP2014/059676
§ 371 (c)(1),
(2) Date: Nov. 12, 2015

(87) PCT Pub. No.: WO2014/184151
PCT Pub. Date: Nov. 20, 2014

(65) Prior Publication Data
US 2016/0116467 A1    Apr. 28, 2016

(30) Foreign Application Priority Data

May 14, 2013    (EP) .................................. 13167722

(51) Int. Cl.
   *G01N 33/543*      (2006.01)
   *A61B 10/00*      (2006.01)
   (Continued)

(52) U.S. Cl.
   CPC .... *G01N 33/54386* (2013.01); *A61B 10/0064* (2013.01); *B01L 3/5023* (2013.01);
   (Continued)

(58) Field of Classification Search
   CPC .......... G01N 33/54386; G01N 33/558; G01N 33/54387; G01N 33/54388;
   (Continued)

(56) References Cited

U.S. PATENT DOCUMENTS 3,552,929 A    1/1971    Fields et al.
5,747,351 A *    5/1998    Hemmati .............. B01L 3/5055
                                                    436/514
(Continued)

FOREIGN PATENT DOCUMENTS

CN      101326442      12/2008
JP      H10185920      7/1998
(Continued)

OTHER PUBLICATIONS

"Patient" Cambridge English Dictionary, retrieved from https://dictionary.cambridge.org/us/dictionary/english/patient on Dec. 10, 2020, 7 pages (Year: 2020).*

(Continued)

*Primary Examiner* — Christopher L Chin
(74) *Attorney, Agent, or Firm* — Leason Ellis LLP

(57) ABSTRACT

The present invention provides a diagnostic kit for detecting the presence or quantity of one or more test analytes within a test sample taken from a body surface of a mammal, the diagnostic kit comprising: a separate insert for a lateral flow device (200, 411) comprising a membrane (201) fixed to a rigid support (202) and, the separate insert being configured to obtain the test sample; a lateral-flow assay device configured (300, 400) to accept the separate insert (200, 411); a securing member (210) configured to releasably attach (211) the separate insert to a body surface of a mammal (213); wherein the securing member (210) comprise an expandable layer (212) configured to apply pressure to the separate insert (200, 411) thereby pressing the separate insert (200, 411) against the body surface of the mammal (213).

9 Claims, 8 Drawing Sheets

(51) Int. Cl.
*B01L 3/00* (2006.01)
*G01N 33/558* (2006.01)
*G01N 33/68* (2006.01)

(52) U.S. Cl.
CPC ....... *G01N 33/558* (2013.01); *G01N 33/6881* (2013.01); *B01L 2200/04* (2013.01); *B01L 2300/0609* (2013.01); *B01L 2300/0825* (2013.01); *B01L 2300/126* (2013.01); *B01L 2400/0406* (2013.01); *G01N 2333/4721* (2013.01); *G01N 2333/5421* (2013.01)

(58) Field of Classification Search
CPC ......... G01N 33/54389; G01N 33/6881; G01N 2333/4721; G01N 2333/5421; A61B 10/0064; B01L 3/5023; B01L 2200/04; B01L 2300/0609; B01L 2300/0825; B01L 2300/126; B01L 2400/0406; A61M 1/984; A61M 1/985; A61F 13/00
USPC ....... 422/400, 401, 420, 421, 425, 426, 430; 435/287.7, 287.9, 970, 805, 810; 436/169, 170, 514, 518, 530, 810; 600/306, 362, 573; 602/53, 54, 58, 78, 602/79; 604/317, 327
See application file for complete search history.

(56) References Cited

U.S. PATENT DOCUMENTS

| | | | | |
|---|---|---|---|---|
| 5,823,983 | A * | 10/1998 | Rosofsky | A61F 13/00034 |
| | | | | 602/41 |
| 5,939,252 | A * | 8/1999 | Lennon | G01N 33/54386 |
| | | | | 422/411 |
| 6,140,136 | A * | 10/2000 | Lee | G01N 33/54366 |
| | | | | 422/423 |
| 6,165,416 | A * | 12/2000 | Chandler | B01L 3/5023 |
| | | | | 422/430 |
| 6,821,788 | B2 * | 11/2004 | Cesarczyk | A61B 10/0045 |
| | | | | 422/412 |
| 2001/0039057 | A1 | 11/2001 | Douglas et al. | |
| 2004/0171173 | A1 | 9/2004 | Eckermann et al. | |
| 2004/0184954 | A1 | 9/2004 | Guo et al. | |
| 2005/0175992 | A1 | 8/2005 | Aberl et al. | |
| 2005/0196318 | A1 * | 9/2005 | Matusewicz | G01N 33/72 |
| | | | | 422/412 |
| 2006/0110285 | A1 * | 5/2006 | Piasio | G01N 21/11 |
| | | | | 422/400 |
| 2007/0134810 | A1 * | 6/2007 | Yang | G01N 33/54366 |
| | | | | 436/514 |
| 2007/0134811 | A1 | 6/2007 | Takeuchi et al. | |

FOREIGN PATENT DOCUMENTS

| | | |
|---|---|---|
| JP | 2004534944 | 11/2004 |
| JP | 2009229342 | 10/2009 |
| WO | WO 2011/008581 | 1/2011 |

OTHER PUBLICATIONS

Marques-Deak et al., Measurement of cytokines in sweat patches and plasma in healthywomen: Validation in a controlled study, Journal of Immunological Methods 315 (2006) 99-109. (Year: 2006).*

* cited by examiner

Figure 1 – cont'd
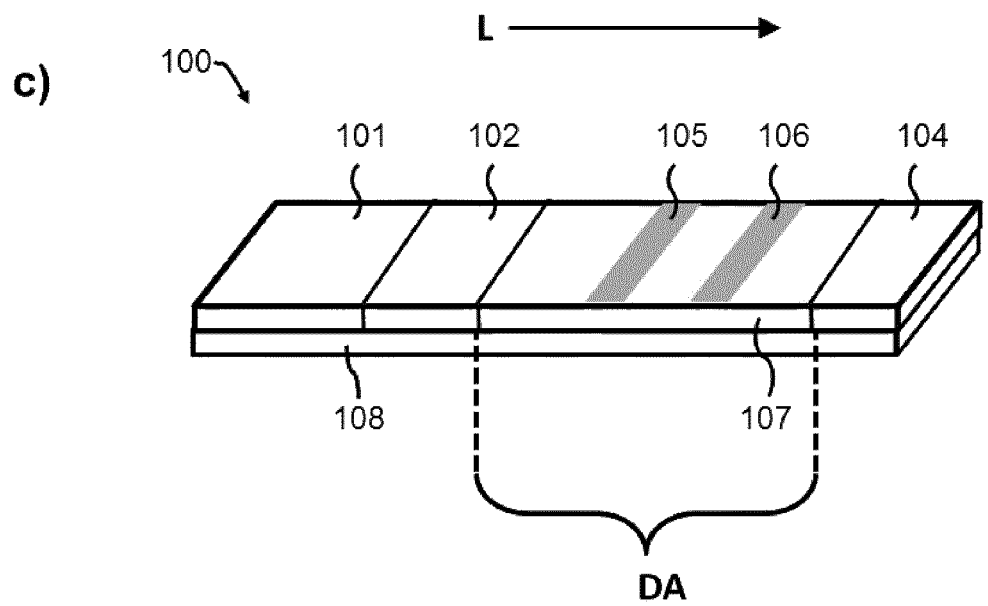
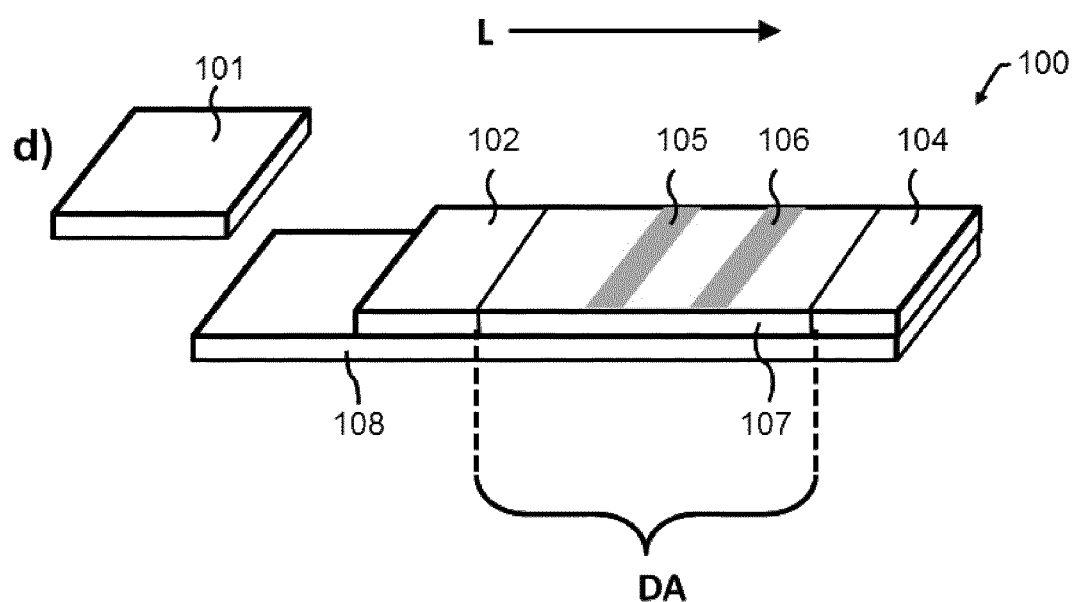

LATERAL FLOW ASSAY DEVICE

CROSS-REFERENCE TO PRIOR APPLICATION

The present application is a U.S. national phase application under 35 U.S.C. § 371 of International Patent Application No. PCT/EP2014/059676, filed May 12, 2014, which claims priority to European patent application No. 13167722.1, filed May 14, 2013, which is incorporated by reference as if expressly set forth in its entirety herein.

FIELD OF THE INVENTION

The present invention relates to diagnostic kits and methods based on lateral flow assay devices for detecting the presence or quantity of one or more test analytes within a test sample taken from a body surface of a mammal; as well as inserts for lateral flow assay devices.

BACKGROUND OF THE INVENTION

Fast development of genomics, transcriptomics, proteomics and regulomics has made it possible to analyze molecular and cellular mechanisms at large scale. One of the important results of these studies has been development of functional genomics and the understanding that cells from different individuals have significant differences in genome structure, gene and protein expression profiles and regulatory mechanisms that control specific cellular functions. This has resulted in an interest in detecting and/or quantifying biomarkers to assess the current state of a mammal by way of presence, absence and/or concentration of one or more biomarkers.

Also there is a need for evaluating how effective treatments are on a personal level, such as in the fields of personalized medicine and personalized skin care.

In relation to personalised medicine, there is a need for point-of-care devices that are useful in the diagnosis or prognosis of a disorder, such as a skin disorder, or in predicting the susceptibility, onset or likely severity of a disorder, such as a skin disorder in an individual; or in predicting the responsiveness of an individual to therapy; or in predicting and/or monitoring relapse after treatment of a particular disorder, such as a skin disorder.

In relation to personalized skin care the claimed effects of anti-wrinkle and anti-aging effects of cosmetic products are typically based on the assumption that these products have similar effect on all individuals. However, this is not the case. Different people and different skin types react differently to cosmetic products, hence the need for point-of-care devices that can determine the effects or responsiveness of an individual to a particular type of skin care product.

One rapid assay method that has been used for point-of-care diagnostic testing, such as a home pregnancy test, is the lateral flow assay method.

One of the challenges faced with lateral flow assay methods are the provision of a sample to test, in particular the provision of a sample form on the skin, and in particular to provide samples from on the skin in a reproducible and/or uniform manner.

In the instance of home pregnancy tests the sample is in most cases urine.

US Patent application 2005/0175992 to Aberl et al. describes a method for the rapid diagnosis of targets in human body fluids. In particular a lateral flow assay method is employed, where a sample is collected non-invasively from eye fluid using a swab member.

The swab member of US 2005/0175992 is not particularly well suited for obtaining analytes from on the skin, in particular when there is a desire to provide a sample in a reproducible and/or uniform manner, or if there is a desire to compare the level of one or more test analytes within the sample with a control sample taken from on the skin at a different place.

Consequently there is a need in the art for kits and methods for obtaining and analysing analytes from the skin, in particular point-of-care devices that allows for rapid detection. There is also a need in the art for sampling methods for point-of-care devices that can provide a sample in a reproducible and/or uniform manner compared to the prior art.

SUMMARY OF THE INVENTION

The present invention was made in view of the prior art described above, and the object of the present invention is to provide point-of-care devices that are particularly well suited for obtaining analytes, from e.g. the human skin surface, in a reproducible and/or uniform manner compared to the prior art, or at least to provide point-of-care devices with alternative ways of obtaining an analyte from on the skin.

To solve the problem, the present invention provides a diagnostic kit for detecting the presence or quantity of one or more test analytes within a test sample taken from a body surface of a mammal, such as the skin surface of a mammal, the diagnostic kit comprising: a separate insert for a lateral flow device (200, 411) comprising a membrane (201), optionally fixed to a rigid support (202), the separate insert being configured to obtain the test sample; a lateral flow assay device configured (300, 400) to accept the separate insert (200, 411); and a securing member (210) configured to releasably attach (211) the separate insert to a body surface of a mammal (213). In some embodiments the membrane has a thickness, a width and a length.

In some embodiments of the present invention the lateral flow device is constructed so as to form a capillary bed, when it is mated with the separate insert, wherein the lateral flow device (100, 500) mated with the separate insert comprise an elution zone (101, 501) and a detection area (DA), as well as one or more of the following: a conjugate pad (102, 502) and a wicking pad (104, 504).

In some embodiments of the present invention the membrane has a thickness equal to 4 mm or less, and a width and a length, both greater than the thickness, wherein the lateral flow device is configured to have a lateral flow direction (L) substantially in the direction of a plane created by the width and the length of the membrane.

In some embodiments of the present invention, the securing member (210) comprise an expandable layer (212) configured to apply pressure to the separate insert (200, 411) thereby pressing the separate insert (200, 411) against the body surface of the mammal (213).

That is, the inventors of the present invention in a first aspect of the invention found that splitting the traditional lateral flow assay device into a separate insert configured to obtain a test sample from e.g. the human skin surface and a lateral flow assay device configured to accept the separate insert is helpful in obtaining samples from on the body surface of a mammal, such as the skin surface of a human being, in particular when combined with a securing member that releasably secures the separate insert to the surface of e.g. the skin.

In preferred embodiments the securing member can apply additional pressure to the separate insert by the actions of an expandable layer that presses the separate insert more firmly to the skin. Where the prior art described above (US 2005/0175992) suggests that a swirling motion of a swab member is sufficient for obtaining a sample, the present inventors have realised that an alternative way of obtaining a sample, and in many cases superior sampling method for obtaining samples from on the skin, is by releasably securing a separate insert to the skin, and applying additional pressure from an expandable layer.

In some embodiments of the present invention, the lateral flow assay device comprises an elution zone (101) and a detection area (DA), and wherein the separate insert is the elution zone (101). That is to say that the separate insert is adapted to fit into the elution zone or sample area. Accordingly, the separate insert is not the detection area (DA).

In some embodiments of the present invention, the lateral flow assay device comprises an elution zone (501) and a detection area (DA), and wherein the separate insert is the detection area (DA). That is to say that the separate insert is adapted to fit into the detection area, which may comprise a detection zone (505) having immobilized one or more affinity molecules. Accordingly, the separate insert is not the elution zone or sample area. This is a modified way of providing a lateral flow assay, in that the one or more test analytes will already be bound to the immobilized affinity molecules once the separate insert is put into the lateral flow assay device.

In some embodiments of the present invention, the separate insert comprise a membrane (201) fixed to a rigid support frame (202).

In some embodiments of the present invention, the rigid support frame (202) covers the perimeter of the membrane (201).

In some embodiments of the present invention, the expandable layer of the securing member contains compressed cellulose, and wherein the expandable layer is not in fluid communication with the separate insert (200, 411).

In some embodiments of the present invention, the detection area (DA) comprise a detection zone (105, 505) containing one or more affinity molecule(s) for selectively retaining one or more test analyte(s) and optionally an indicator zone (106, 506) containing one or more affinity molecule(s) for selectively retaining one or more indicator affinity molecule(s).

In some embodiments of the present invention, wherein the one or more test analyte(s) are selected from the list consisting of: chemokines, interleukins, growth factors, hormones, enzymes, and other molecules present on the skin of a mammal, such as selected from the list consisting of: IL-1a, IL-1b, IL-1RA, IL-8, CCL-2, CCL-5, CCL-27, CXCL-1, CXCL-2, CXCL-9, Trappin2/Elafin, hBD-1, hBD-2, VEGF, and TSLP.

In another aspect of the present invention, there is provided an insert for a lateral flow assay device (200, 411) comprising a membrane (201) fixed to a rigid support frame (202), the separate insert being configured to obtain the test sample from a body surface of a mammal (213).

In some embodiments of the present invention, the membrane has a thickness equal to or less than 4 mm, and a width and a length both greater than the thickness.

In some embodiments of the present invention, the rigid support frame covers the perimeter of the membrane.

In some embodiments of the present invention, the insert additionally comprising a securing member (210) configured to releasably attach (211) the insert to a body surface of a mammal (213).

In some embodiments of the present invention, the insert is the detection area (DA) of the lateral flow assay device comprising a detection zone (105, 505) containing one or more affinity molecule(s) for selectively retaining one or more test analyte(s).

In some embodiments of the present invention, the membrane is water permeable from the side facing away (i.e. the opposing side) from the skin surface to which the membrane is configured to attach.

In some embodiments of the present invention wherein the one or more test analyte(s) are selected from the list consisting of: chemokines, interleukins, growth factors, hormones, enzymes, and other molecules present on the skin of a mammal, such as selected from the list consisting of: IL-1a, IL-1b, IL-1RA, IL-8, CCL-2, CCL-5, CCL-27, CXCL-1, CXCL-2, CXCL-9, Trappin2/Elafin, hBD-1, hBD-2, VEGF, and TSLP.

In another aspect of the present invention, there is provided a method for detecting the presence or quantity of one or more test analytes, the method comprising the following steps:

releasably attaching to a body surface of a mammal a separate insert for a lateral flow device (200, 411) comprising a membrane (201) fixed to a rigid support (202) and, the separate insert being configured to obtain the test sample;

leaving the separate insert (200) on the body surface of the mammal (213) for at least 5 minutes;

securing the separate insert containing the test sample in a lateral flow assay device adapted to receive the separate insert (300, 400);

developing the lateral flow assay device.

In some embodiments of the present invention, the separate insert (200, 411) is releasably attached to the body surface by a securing member (210) configured to releasably attach (211) the separate insert to a body surface of a mammal (213), and where the securing member comprises an expandable layer (212) that is activated between steps a) and b) thereby generating a force pressing the separate insert against the body surface.

In some embodiments of the present invention, the lateral flow assay device comprises an elution zone (101) and a detection area (DA), and wherein the separate insert is the elution zone (101).

In some embodiments of the present invention, the lateral flow assay device comprises an elution zone (101) and a detection area (DA), and wherein the separate insert is the detection area (DA).

In some embodiments of the present invention, the body surface of the mammal is the skin of a human being.

In some embodiments of the present invention, the lateral flow assay device is constructed so as to form a capillary bed, when it is mated with the separate insert, wherein the lateral flow device (100, 500) mated with the separate insert comprise an elution zone (101, 501) and a detection area (DA), as well as one or more of the following: a conjugate pad (102, 502) and a wicking pad (104, 504).

In some embodiments of the present invention, the membrane has a thickness equal to 4 mm or less, and a width and a length, both greater than the thickness, wherein the lateral flow device is configured to have a lateral flow direction (L)

substantially in the direction of a plane created by the width and the length of the membrane.

BRIEF DESCRIPTION OF THE DRAWINGS

Certain illustrative embodiments are described in more detail below with reference to the accompanying figures in which:

In FIG. 1a a lateral flow strip (100) is shown with a sample pad (101), an conjugate pad (102), a detection zone (105) and an indicator zone (106), both zones immobilized on porous support (107), a wicking pad (104) and a backing material (108). "L" shows the direction of the lateral flow and the area "DA" defines the detection area. FIG. 1b illustrates the lateral flow strip, where the sample pad (101) is detached from the remaining lateral flow strip. FIG. 1c shows an alternative embodiment of FIG. 1a, where the sample pad (101); conjugate pad (102); detection zone (105) and indicator zone (106) on porous support (107); and wicking pad (104) is adjoining or overlapping, and placed on a backing material (108). FIG. 1d illustrates the lateral flow strip of FIG. 1c, where the sample pad (101) is detached from the remaining lateral flow strip.

In FIG. 2a is shown a separate insert (200) for a lateral flow assay device with a membrane (201) fixed to a rigid support (202). FIG. 2b shows one embodiment of the same separate insert (200), where the bottom of the membrane (201) that makes contact with the body surface of the mammal is shown. FIG. 2c shows a securing member (210) configured to releasably attach (211) to the body surface of a mammal with an expandable layer (212). FIG. 2d shows an embodiment where a separate insert is releasably attached to the body surface of a mammal (213) by securing member (210), and where the top side of the expandable layer (212) is shown.

In FIG. 3a a lateral flow assay device (300) with housing (310) is shown with a separate insert (200), and sample pad cover (312) in an open position showing sample port (313) allowing for addition of liquid for the development of the lateral flow device, and a reaction window (311) allowing for visual detection of reactions in the detection zone and indicator zone. FIG. 3b shows a cross-sectional view of an embodiment of the present invention, where the lateral flow assay housing (310) contains a separate insert (200) in place in the position of a sample pad (101) with a sample pad cover (312) in closed position showing the sample port (313). The separate insert is in fluid communication with a porous support (309), that again is in fluid communication with a conjugate pad (302), again in fluid communication with a porous membrane (307) which has a detection zone and indicator zone immobilized (105, 106, not shown), and a wicking pad (304). Finally a reaction window (311) allows for visual inspection of the detection area ("DA").

In FIG. 4a a lateral flow assay device (400) with housing (410) is shown with a separate insert (411) and a sample port (413) allowing for addition of liquid for development of the lateral flow device. FIG. 4b shows a cross-sectional view of an lateral flow assay device (400) according to one embodiment of the present invention, where a lateral flow assay housing (410) contains a separate insert (411) being inserted at the position of a detection area ("DA"). A sample pad (401), sample port (413) and wicking pad (404) is shown, and once the separate insert (411) is fully inserted, it will bring the sample pad in fluid connection with the wicking pad (404) through the separate insert (411). FIG. 4c shows a lateral flow assay device (400) where a separate insert is fully inserted. A detection zone (405) and indicator zone (406) are shown. FIG. 4d shows a cross-sectional view of a lateral flow assay device (400) according to one embodiment of the present invention, where a separate insert (411) is fully inserted and where the sample pad (401), separate insert (411) with a detection zone (405) and an indicator zone (406) is in fluid communication with a wicking pad (404).

In FIG. 5a a lateral flow strip (500) is shown with a sample pad (501), a conjugate pad (502), a detection zone (505) and an indicator zone (506), both zones immobilized on porous support (507), a wicking pad (504) and optionally a backing material (508). "L" shows the direction of the lateral flow and the area "DA" defines the detection area. FIG. 5b illustrates the lateral flow strip, where the detection zone (505) and indicator zone (506) immobilized on porous support (507) is detached from the remaining lateral flow strip.

FIG. 6b shows that using a sample pad placed on the skin, IL-8 and hBD-1 can be detected from the skin surface.

FIG. 7b shows that using detection area (DA) as the "sampling area", the analytes hBD-1 and IL-8 can be detected from the skin surface.

Figure 1:
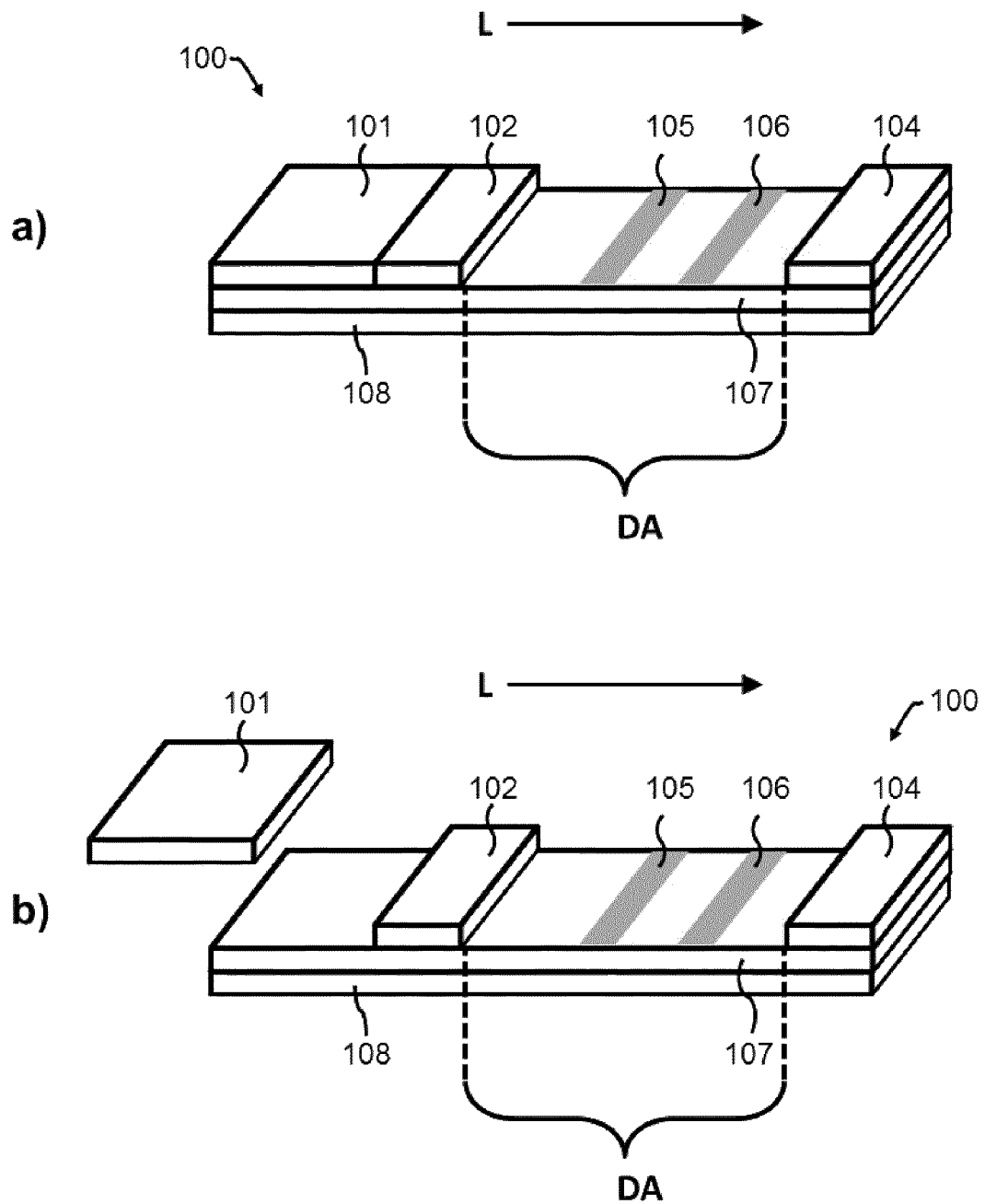
FIG. 1 shows perspective views of different embodiments, of the present invention, of a lateral flow assay strip (100).
Figure 2:
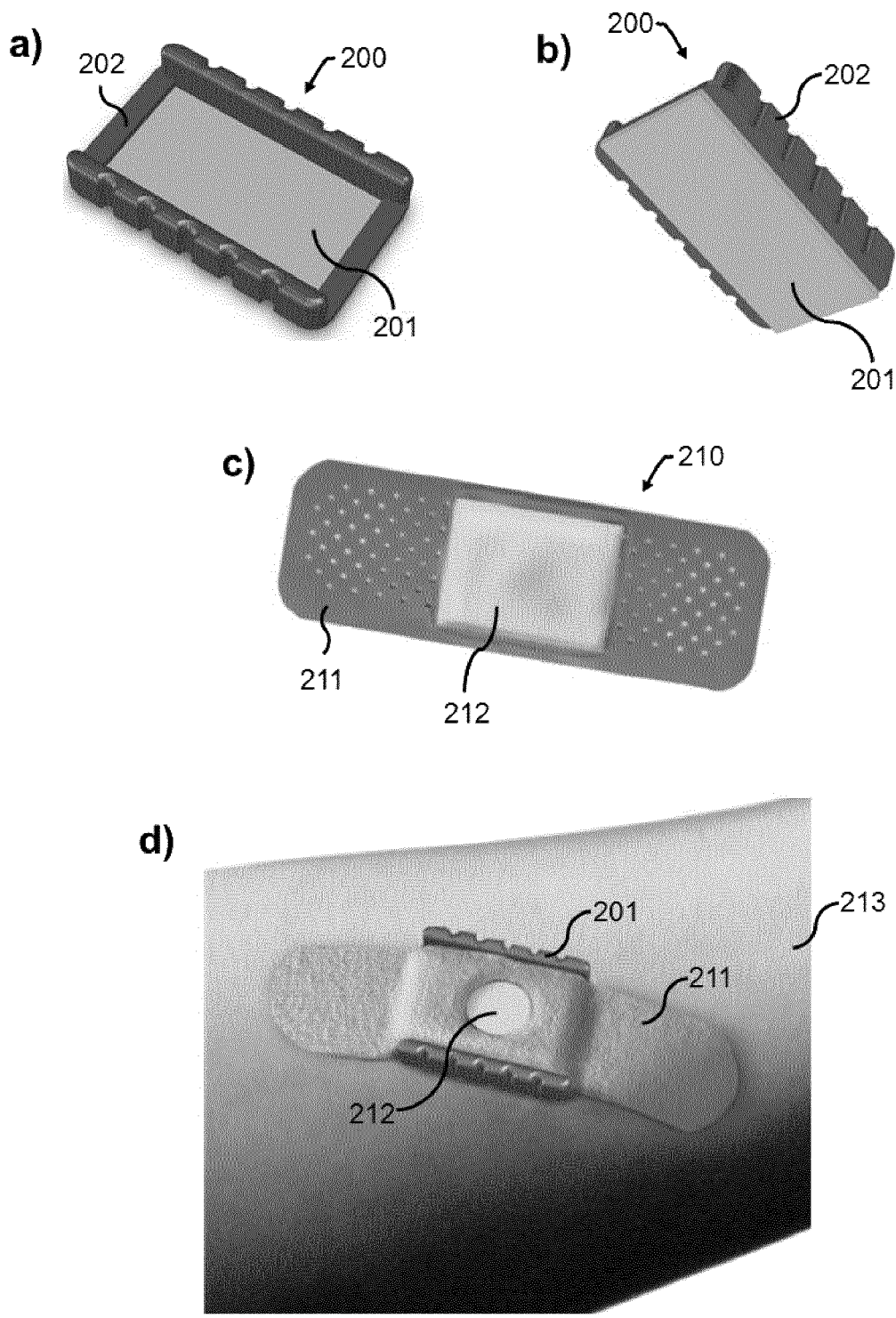
FIG. 2 shows in an embodiment of the present invention different views of a separate insert (200), a securing member (210), and the securing member holding the separate insert on the skin of a mammal.

It will be recognized by the person of ordinary skill in the art, given the benefit of this disclosure that certain features shown in FIGS. 1-5 are not necessarily drawn to scale. The dimensions and characteristics of some features in the figures may have been enlarged, distorted or altered relative to other features in the figures to facilitate a better understanding of the illustrative examples disclosed herein.

It will further be recognized by the person of ordinary skill in the art that the individual features of the figures may be interchanged to obtain further embodiments.

DETAILED DESCRIPTION OF THE INVENTION

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose.

Lateral flow assays may be employed in point-of-care devices to detect the presence or absence of one or more test analytes within a test sample. The readout may be done visually, i.e. presence or absence of a one or more coloured test lines also referred to as test stripes in a detection zone (105), and the confirmation/validation of the test may be done by the presence and/or absence of one or more coloured indicator lines/stripes in an indicator zone (106). The test may be qualitative (presence or absence) as well as quantitative, and the detection/quantification may be aided by reading equipment, or can be purely visual detection by the eye of the user of the lateral flow assay.

If desired, an reading equipment, such as an optical reader may be used in some embodiments to measure the intensity of the probes. The actual configuration and structure of the optical reader may generally vary depending on the probes, which are to be measured. For example, optical detection techniques that may be utilized include, but are not limited to, luminescence (e.g. fluorescence, phosphorescence, etc.), absorbance (e.g. fluorescent or non-fluorescent), diffraction, and so on. Qualitative, quantitative, or semi-quantitative determination of the presence or concentration of an analyte may be achieved in accordance with the present invention. For instance, the amount of the analyte may be quantitatively or semi-quantitatively determined by using the intensities of the signals produced by detection probes bound at the detection zone (105) and the indicator zone (106).

Lateral flow assays may be based on a capillary bed (such as porous paper or sintered polymer), or in most instances it may be based on a series of capillary beds in fluid communication with each other. The capillary beds have the capacity to transport fluid by action of capillary forces. In some embodiments of the present invention, the lateral flow assay is constructed so as to form a capillary bed.

The first element, the sample pad (101) acts as a sponge and holds the test sample. Once it is soaked, the test sample, containing one or more test analytes, will migrate to a conjugate pad (102), which contains one or more indicator affinity molecule(s), such as affinity molecules tagged with detection probe designed to bind to the one or more test analytes within the test sample. The test sample and one or more affinity molecules are mixed and the one or more affinity molecules having affinity for one or more test analytes within the test sample will bind to each other while migrating further to a detection area (DA) that may contain a detection zone (105), and may contain an indicator zone (106), both with one or more stripes, where another set of one or more affinity molecules have been immobilized. By the time the test sample mixed with the affinity molecule(s) from the conjugate pad reaches the detection area (DA), the one or more analytes in the test sample will have been bound to the affinity molecule(s) from the conjugate pad. This complex will then in turn be bound by the affinity molecule(s) on the stripe(s) in the detection zone (105). After a while, when more and more fluid has passed the detection zone, detection probes accumulate, and the stripe changes color. The detection probes may e.g. be gold or latex particles conjugated to the affinity molecule(s) to prepare affinity molecules tagged with detection probes. The detection area (DA) may also comprise an indicator zone (106) which can function as a control to verify that the lateral flow assay has been conducted properly. Such indicator zone (106) may also comprise one or more stripes with affinity molecules immobilized that only binds to the affinity molecule(s) tagged with detection probes from the conjugate pad, whereas the affinity molecule(s) in the detection zone (105) bind to the complex between the analyte(s) and the indicator affinity molecule(s), such as the affinity molecule(s) tagged with detection probes from the conjugate pad. After passing the detection area (DA) the fluid enters the wicking pad (104), which generally receives fluid that has migrated through the entire capillary bed (101, 102, DA, 104—also represented by 107). The wicking pad may assist in promoting capillary action and fluid flow from the sample pad (101), conjugate pad (102) through the detection area (DA).

The lateral flow assay strip may optionally comprise a backing layer (108) and/or housing (310, 410), which is liquid-impermeable so that fluid flowing through lateral flow assay strip does not leak through the backing layer (108). Examples of suitable materials for the support include, but are not limited to, glass; polymeric materials, such as polystyrene, polypropylene, polyester, polybutadiene, polyvinylchloride, polyamide, polycarbonate, epoxides, methacrylates, and polymelamine.

The detection zone (105) may be located upstream or downstream of the indicator zone (106). The lines or stripes in the detector zone or indicator zone may be disposed in a direction that is substantially perpendicular to the flow of the test sample. In some embodiments the lines may be in a direction that is substantially parallel to the flow of the test sample. The lines or stripes in the detection zone (105) or indicator zone (106) does not need to be lines or stripes, and can also be other shapes, such as e.g. dots or patterns.

In one aspect of the present invention there is provided a diagnostic kit for detecting the presence or quantity of one or more test analytes within a test sample taken from a body surface of a mammal, the diagnostic kit comprising: a separate insert for a lateral flow device (200, 411) comprising a membrane (201), which may be fixed to a rigid support (202), the separate insert being configured to obtain the test sample; a lateral flow assay device configured (300, 400) to accept the separate insert (200, 411); and a securing member (210) configured to releasably attach (211) the separate insert to a body surface of a mammal (213).

In general the present invention is directed to a diagnostic kit that provides an integrated system for detecting the presence or absence of one or more test analytes within a test sample, over a broad range of possible concentrations of the one or more test analytes. In some embodiments the quantity of the one or more test analytes are also detected in a quantitative assay. The diagnostic kit employs a lateral flow assay device (300, 400) and a separate insert (200, 411) and one or more assay reagents for detecting the one or more test analytes within the test sample. The assay reagents include affinity molecule(s) tagged with detection probes that are capable of producing a detection signal representing the presence or quantity of the one or more test analyte(s) in the test sample. One way of quantifying one or more of the test analyte(s) is by preparing suitable standard curves using known concentrations of the one or more test analyte(s).

In some embodiments of the present invention, the one or more test analyte(s) are selected from the list consisting of: chemokines, interleukins, growth factors, hormones, enzymes, and other molecules present on a body surface of a mammal, such as the skin of a mammal. Specific test analytes may include one or more selected from the list consisting of: IL-1 a, IL-1b, IL-1RA, IL-8, CCL-2, CCL-5, CCL-27, CXCL-1, CXCL-2, CXCL-9, Trappin2/Elafin, hBD-1, hBD-2, VEGF, and TSLP.

The present invention is suited for the detection of any molecule that is present on the skin of a mammal, which may be chemokines, interleukins, growth factors, hormones or enzymes. Likewise the present invention is also suited for the detection of drugs as well as metabolites thereof, insofar that they are excreted on the skin of a mammal. This detection of drugs covers both drugs taken for medicinal and/or cosmetic purposes as well as drugs taken for recreational purposes.

The test sample is taken from a body surface of a mammal using a separate insert for a lateral flow device. The separate insert comprise a membrane (201), which may be fixed to a rigid support (202).

The rigid support (202) may be used to stabilise the membrane (201) so that it does not bend or fold, and it may be used to ease the handling of the separate insert by allowing it to fit, or click in place in the lateral flow assay device (300), such as for example screwing in place. In some embodiments the rigid support covers the perimeter of the membrane, such as e.g. depicted in FIG. 2.

The membrane is configured to obtain the test sample, which means that the membrane should be capable of absorbing the test sample, and any material capable of doing so may be suitable. The materials used for the membrane may include, but are not limited to, natural, synthetic or naturally occurring materials that are synthetically modified, such as polysaccharides (e.g. cellulose materials such as paper and cellulose derivatives such as cellulose acetate and nitrocellulose), polyether sulfone, polyethylene, nylon polyvinylidene fluoride (PVDF), polyester, polypropylene, cotton, or cloth. In some embodiments the membrane is non-adhesive, which will minimize the amount of skin cells transferred to the membrane. The materials used for the rigid support may include, but are not limited to, plastic materials, composites, metals or metal alloys.

The membrane may be sheet like. The membrane may have a thickness equal to or less than 4 mm (such as less than 4, 3, 2, 1 mm), and a width and a length both greater than the thickness. In some embodiments the width and length of the membrane are both greater (e.g. 3, 4, 5, 6, 7, 8, 9, 10, 50 times greater or up to 4, 5, 6, 7, 8, 9, 10, 50 times greater) than the thickness. In some embodiments the membrane is a square, such as a rectangle, and in some embodiments the membrane is circular. If the membrane is an irregular shape, i.e. different from a square or rectangle, then the width, length and thickness refers to the maximum values for such an irregular shape. For example the width of a circle will be the diameter. Examples of widths and lengths may be 4, 5, 6, 7, 8, 9, 10, 11, 12, 13, 14, 15, 16, 17, 18, 19, 20, 21, 22, 23, 24, 25, 26, 27, 28, 29, 30, 35, 40 mm, such as e.g. range of widths and lengths from 5-30 mm.

The test sample is taken from a body surface of a mammal, and comprise the one or more test analyte(s). The test sample is obtained by diffusion of the sample from the body surface of a mammal to the membrane. The sampling may be assisted by wetting the membrane with a fixed volume of fluid, either while it is attached at the sampling site on the body surface or before it is attached to the sampling site on the body surface.

Figure 3:
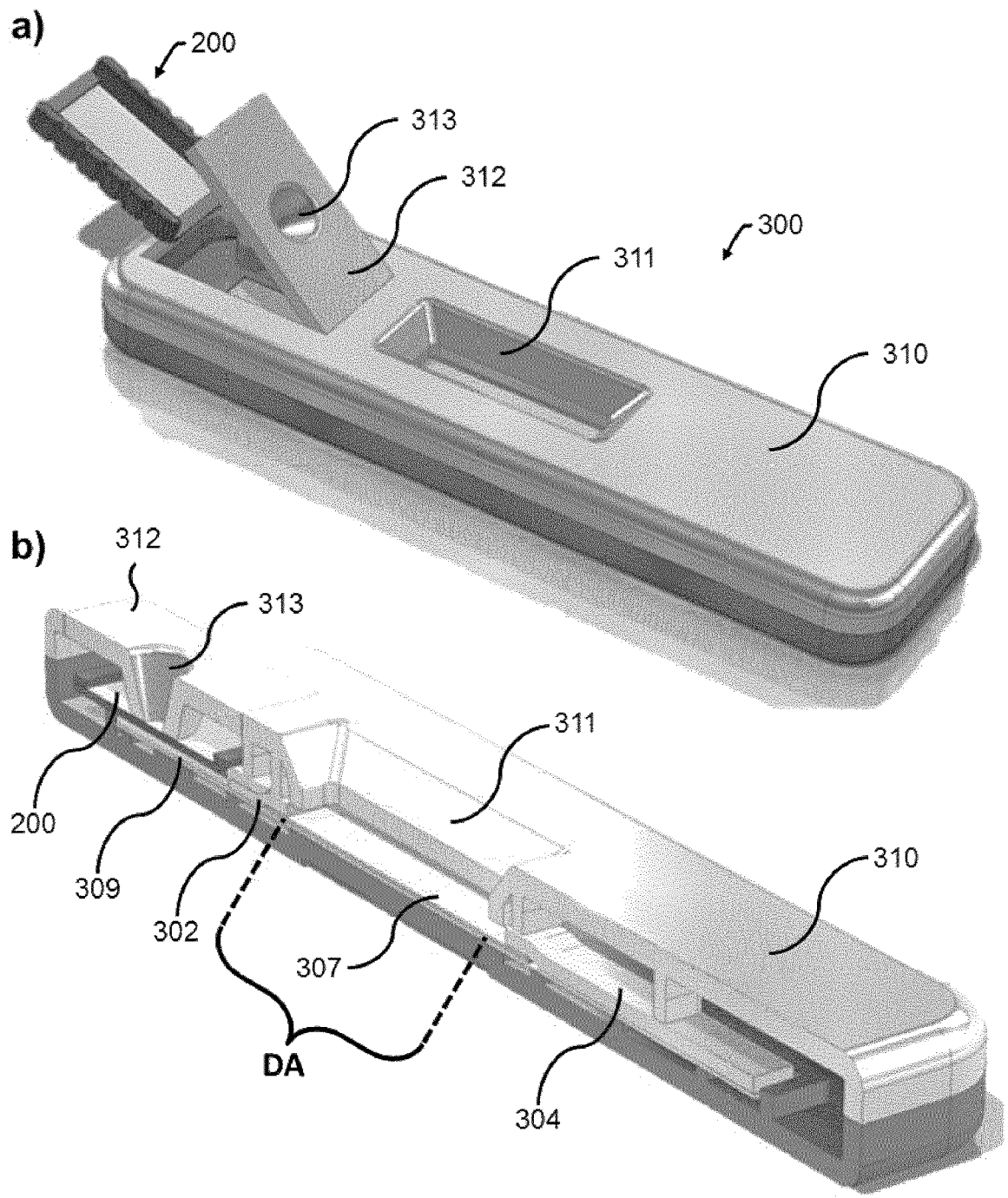
FIG. 3 shows one embodiment according to the present invention.

In some embodiments the membrane is water permeable from the side facing away from the skin surface to which the membrane is configured to attach. This may allow wetting of the membrane with a fixed volume of fluid while it is attached, as well as it may allow the addition of a liquid for the development of the lateral flow device, when e.g. the membrane functions as part of the elution zone, as shown in FIG. 3, i.e. it allows wetting of the membrane from the side facing away from the skin surface to which the membrane is configured to attach.

In preferred embodiments the body surface is the skin, such as the skin of a human body, and in preferred embodiments, the mammal is a human body.

After the test sample has been transferred to the membrane, the separate insert is then inserted into a lateral flow assay device configured (300, 400) to accept the separate insert (200, 411).

In some embodiments of the present invention, the lateral flow device is constructed so as to form a capillary bed, when it is mated with the separate insert, wherein the lateral flow device (100, 500) mated with the separate insert comprise an elution zone (101, 501) and a detection area (DA), as well as one or more of the following: a conjugate pad (102, 502) and a wicking pad (104, 504).

In some embodiments of the present invention, the lateral flow device is configured to have a lateral flow direction (L) substantially in the direction of a plane created by the width and the length of the membrane. Substantially in the direction of the plane encompasses both adjoining as well as overlapping, such as partially overlapping of the membrane with the other elements of the lateral flow device, see e.g. FIG. 1, where the elements (101. 102, 107, 104) of the lateral flow device is being depicted as being adjoining. See e.g. FIG. 3b, where the separate insert (200) is partially overlapping with a porous support (309), a conjugate pad (302), porous membrane (307) and a wicking pad (304). Had the porous support (309) been entirely overlapping with the separate insert (200) the lateral flow direction (L) from the sample pad to the detection area (DA) would still have been substantially in the direction of the plane created by the width and the length of the membrane, as opposed to perpendicular to that plane.

Many possibilities for mating a separate insert with a lateral flow device exist, and in preferred embodiments the membrane part of the insert is prepared such that it will fit in the same place of the lateral flow assay device thereby increasing reproducibility. One way of placing the membrane part of the insert in the same position in a reproducible manner is to fix the membrane to a rigid support.

When desiring to obtain the test sample in a reproducible and uniform manner, from a particular spot on the body surface, the insert is releasably attached (211) to the body surface preferably using a securing member (210). By attaching the insert to the body surface in a releasable manner, it becomes possible to sample a particular area, defined by the size of the membrane of the insert, for a particular duration of time. This is advantageous when wanting to compare the levels of particular test analytes in a test sample taken from e.g. a lesional area of the skin with particular test analytes in a test sample taken from e.g. a healthy or non-lesional area of the skin in a reproducible manner, where the same skin area size is sampled for the same duration. Releasably attaching the insert provides advantages over swabbing an area with a swabbing member, as swabbing is done over a less accurately defined area, and in a non-reproducible manner, when it comes to sample-to-sample variation, meaning that it becomes difficult to prepare test sample from e.g. a non-lesional skin using swabbing with the same sample size as a test sample obtained by swapping a lesional area of the skin. Consequently, releasably attaching excludes swabbing.

One example of lesional skin, may be inflamed skin, and one example of non-lesional skin may be non-inflamed skin, for instance lesional psoriatic skin and non-lesional psoriatic skin.

In some embodiments the securing member is a strip of adhesive material.

When desiring to improve the reproducibility and uniformity when obtaining the test sample, the securing member (210) may comprise an expandable layer (212) configured to apply pressure to the separate insert (200, 411) thereby pressing the separate insert (200, 411) against the body surface of the mammal (213). One way of configuring the expandable layer to apply pressure to the separate insert is by placing it between the separate insert and the securing member. The expandable layer (212) is a layer that can be expanded so as to apply pressure to the membrane (201) of the separate insert (200, 411). Examples of an expandable layer are an inflatable material, such as an inflatable pouch, a spring operated device or a swellable material. In some embodiments the material is compressed cellulose, which will swell upon contact with a liquid, such as an aqueous solution, thereby applying pressure to the membrane (201), which will be pressed tightly against the skin of the mammal. It can be seen from the table in example 3 that the standard deviation of obtaining a sample from on the skin using a separate insert with an expandable layer is improved compared to not using an expandable layer. In some embodiments of the present invention, the expandable layer is not in fluid communication with the separate insert (200, 411), as there could be some risk of transferring part of the test sample to the expandable layer, if the expandable layer is made out of e.g. compressed cellulose in fluid communication with the membrane. In some embodiment there is an inert backing layer between the expandable layer and the membrane, which will not allow the test sample to diffuse into the expandable layer.

Accordingly in some embodiments of the present invention, there is provided an insert for a lateral flow assay device (200, 411) comprising a membrane (201) fixed to a rigid support frame (202), the separate insert being configured to obtain the test sample from a body surface of a mammal (213), and in some embodiments of the present invention, the insert additionally comprising a securing member (210) configured to releasably attach (211) the insert to a body surface of a mammal (213).

The embodiments described so far has been described with reference to an embodiment of the present invention of the lateral flow assay device comprising an elution zone (101) and a detection area (DA), and where the separate insert is the elution zone (101). That is to say that the separate insert is adapted to fit into the elution zone or sample area.

However, the present invention also covers embodiments of the lateral flow assay device comprising an elution zone (501) and a detection area (DA), and wherein the separate insert is the detection area (DA). That is to say that the separate insert is adapted to fit into the detection area, which may comprise a detection zone (505) having immobilized one or more affinity molecules. This is a modified way of providing a lateral flow assay, in that the one or more test analytes will already be bound to the immobilized affinity molecules once the separate insert is put into the lateral flow assay device.

In this embodiment, where the separate insert is the detection area (DA), the lateral flow assay device will function slightly different, in that the one or more test analytes will already be bound to the affinity molecules immobilized in the detection zone (405) when the test sample is obtained from a body surface of a mammal. The developing of the lateral flow assay by adding fluid to the sample pad (401) will then transport the affinity molecule(s) tagged with detection probes from the conjugate pad over the detection area (DA) and they will bind to the one or more test analytes already bound to the affinity molecules immobilized in the detection zone thereby detecting the presence or quantity of the one or more test analytes in the test sample.

In some embodiments of the present invention, the detection area (DA) comprise a detection zone (105, 505) containing one or more affinity molecule(s) for selectively retaining one or more test analyte(s) and optionally an indicator zone (106, 506) containing one or more affinity molecule(s) for selectively retaining one or more indicator affinity molecule(s), such as affinity molecule(s) tagged with detection probes from the conjugate pad.

Affinity molecules are molecules which predominantly bind to one or more analyte(s) thereby selectively retaining such analyte(s) of interest. Affinity molecules in general are molecules that have a larger affinity for a particular analyte or class of analytes than other analytes. Most notable examples of such molecules are antibodies (polyclonal and/or monoclonal, and fragments thereof), aptamers, and receptors, as well as other engineered protein scaffolds such known as AdNectin, Affibody, Anticalin, Knottin, DARPin and Kunitz, as well as organic and/or polymeric scaffolds.

In another aspect of the present invention, there is provided a method for detecting the presence or quantity of one or more test analytes, the method comprising the following steps:

releasably attaching to a body surface of a mammal a separate insert for a lateral flow device (200, 411) comprising a membrane (201) fixed to a rigid support (202) and, the separate insert being configured to obtain the test sample;

leaving the membrane of the separate insert (200) on the body surface of the mammal (213) for at least 5 minutes or for a duration ending when a sufficient amount of test sample has been obtained;

securing the separate insert containing the test sample in a lateral flow assay device adapted to receive the separate insert (300, 400);

developing the lateral flow assay device.

In some embodiments of the present invention, the separate insert (200, 411) is releasably attached to the body surface by a securing member (210) configured to releasably attach (211) the separate insert to a body surface of a mammal (213), and where the securing member comprises an expandable layer (212) that is activated between steps a) and b) thereby generating a force pressing the separate insert against the body surface.

The membrane layer of the separate insert will be attached to the skin for the duration of the sampling period, which ends when a sufficient amount test sample has been obtained. In some instances it will be sufficient to have the membrane layer attached to the skin for at least 1 minute, such as at least 5 minutes, at least 10 minutes, at least 15 minutes, at least 20 minutes, at least 30 minute, at least 40 minutes, at least 50 minutes, at least 60 minutes, such as up to 5 minutes, up to 10 minutes, up to 15 minutes, up to 20 minutes, up to 30 minute, up to 40 minutes, up to 50 minutes, up to 60 minutes, such as up to 24 hours. It is desirable to keep the sampling time as short as possible, as it will allow for a faster detection. It is envisaged that the present sampling method should be sensitive enough to allow for a sampling time, where the membrane is attached to the skin, or in fluid communication with the skin to be between 1 and 30 minutes, in particular between 15 and 30 minutes.

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

The terms "comprising", "comprise" and "comprises" herein are intended by the inventors to be optionally substitutable with the terms "consisting of", "consist of" and "consists of", respectively, in every instance.

EXAMPLES

Example 1

Detecting IL-8 and hBD-1 with the Device According to FIG. 3

This is an example showing that a separate insert of a sample pad (200) separate from the lateral flow assay device (300) can be used in a lateral flow assay (FIG. 3) to detect IL-8 and hBD-1 from the human skin.

Materials

| | |
|---|---|
| Capture antibodies: | 100 ug/ml in 1xPBS: Rabbit anti-Human BD-1, and Goat anti-Human CXCL8/IL-8 |
| Detector antibodies: | Conjugated to 40 nm Colloidal Gold at 10 ug/mL: Rabbit anti-Human BD-1, and Mouse anti-Human CXCL8/IL-8 |
| Antigens: | Various levels 0-50 ng/ml in Running buffer Recombinant Human BD-1, and Recombinant Human CXCL8/IL-8 |
| Running buffer: | 25 mM Tris, 1% Pentasodium Tripolyphosphate, 0.1% Sodium Azide, 0.1% TritonX-405, 2 mM EDTA, 0.5% Sodium Casein, pH 8.0 |
| Analysis membrane (307): | Sartorius CN140, with capture antibodies, blocked with blocking buffer: 10 mM Sodium Phosphate, 0.1% Sucrose, 0.1% BSA, 0.2% PVP-40, pH 7.2 |
| Wicking pad (304, 104): | Millipore CO95 |
| Conjugate pad (302, 102): | Millipore G041, Blocking buffer: 10 mM Borate, 3% BSA, 1% PVP-40, 0.25% Tritonx-100, pH 8.0 |
| Sample pad (collection pad) (200): | Millipore G041 |

Calibration of Test Sensitivity

Figure 6:
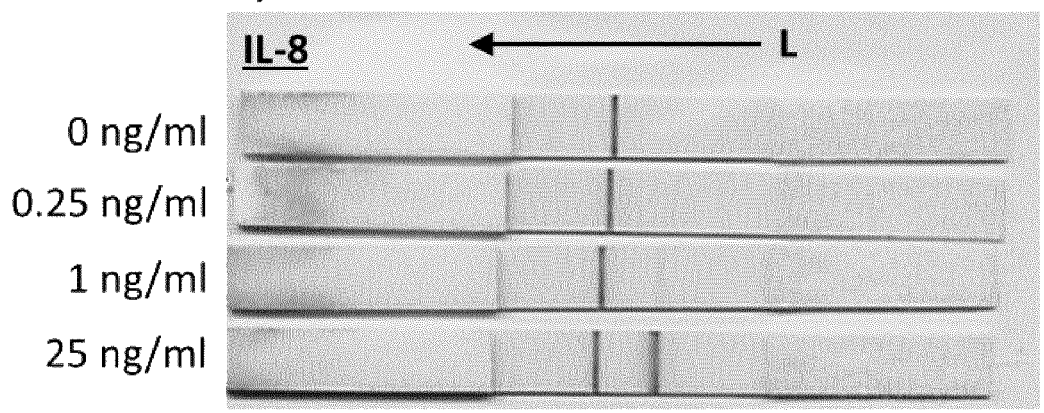
FIG. 6 shows the sensitivity of a lateral flow assay device according to example 1, where in FIG. 6a different concentrations of analytes added directly to sample pads were analysed. Controls (left) and analytes (right) shows this a level of visual detection of IL-8 detection to be around 1 ng/ml and that the level of visual detection of hBD-1 to be around 0.25 ng/ml.
Figure 6:
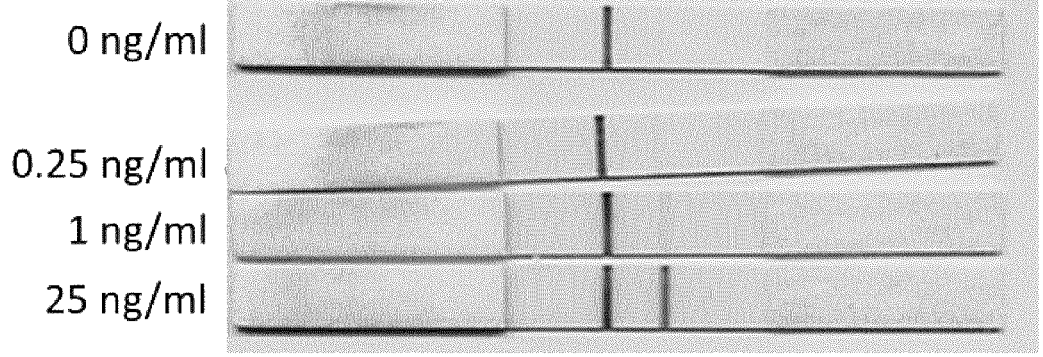
Figure 6:
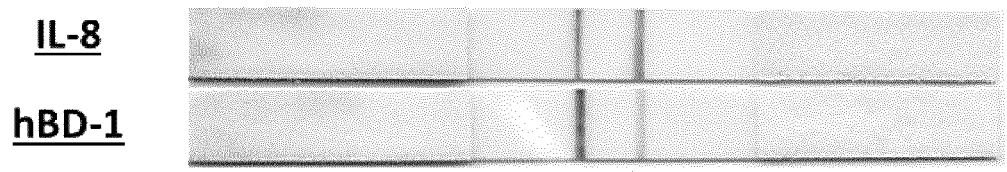

Analytes IL-8 and hBD1 were diluted in running buffer to concentrations 0.25, 1 and 25 ng/ml and used for determining sensitivity for this particular setup (FIG. 6a). For testing, analytes were added to the sample pad (50 µl) following assembly of the analysis cassette and adding 100 µl of running buffer.

The lateral flow strips of FIG. 6a shows the level of visual detection of IL-8 to be around 1 ng/ml and that the level of visual detection of hBD-1 to be around 0.25 ng/ml.

To analyze IL-8 and hBD-1 from the skin, a sample pad (200) was wetted with 25 µl of milliQ water and placed in contact with a lesional area of contact dermatitis skin for 15 minutes, inserted into the lateral flow assay cassette (310) and developed by adding 100 µl of running buffer.

The lateral flow strip is shown in FIG. 6b where it can be seen that IL-8 and hBD-1 (right) can be detected from a sample obtained from the skin surface. Controls are shown (left).

Example 2

Figure 4:
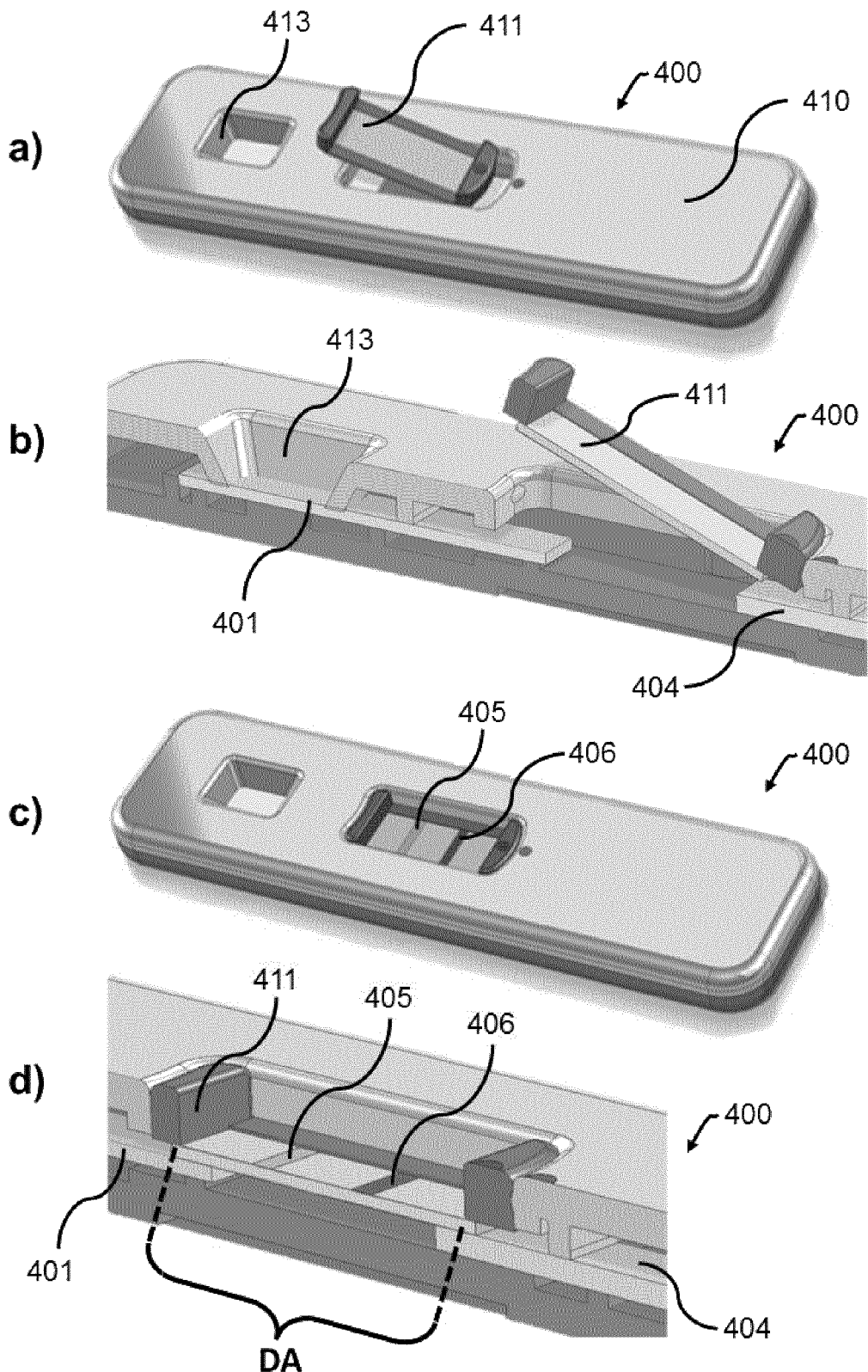
FIG. 4 shows an embodiment according to the present invention.
Figure 5:
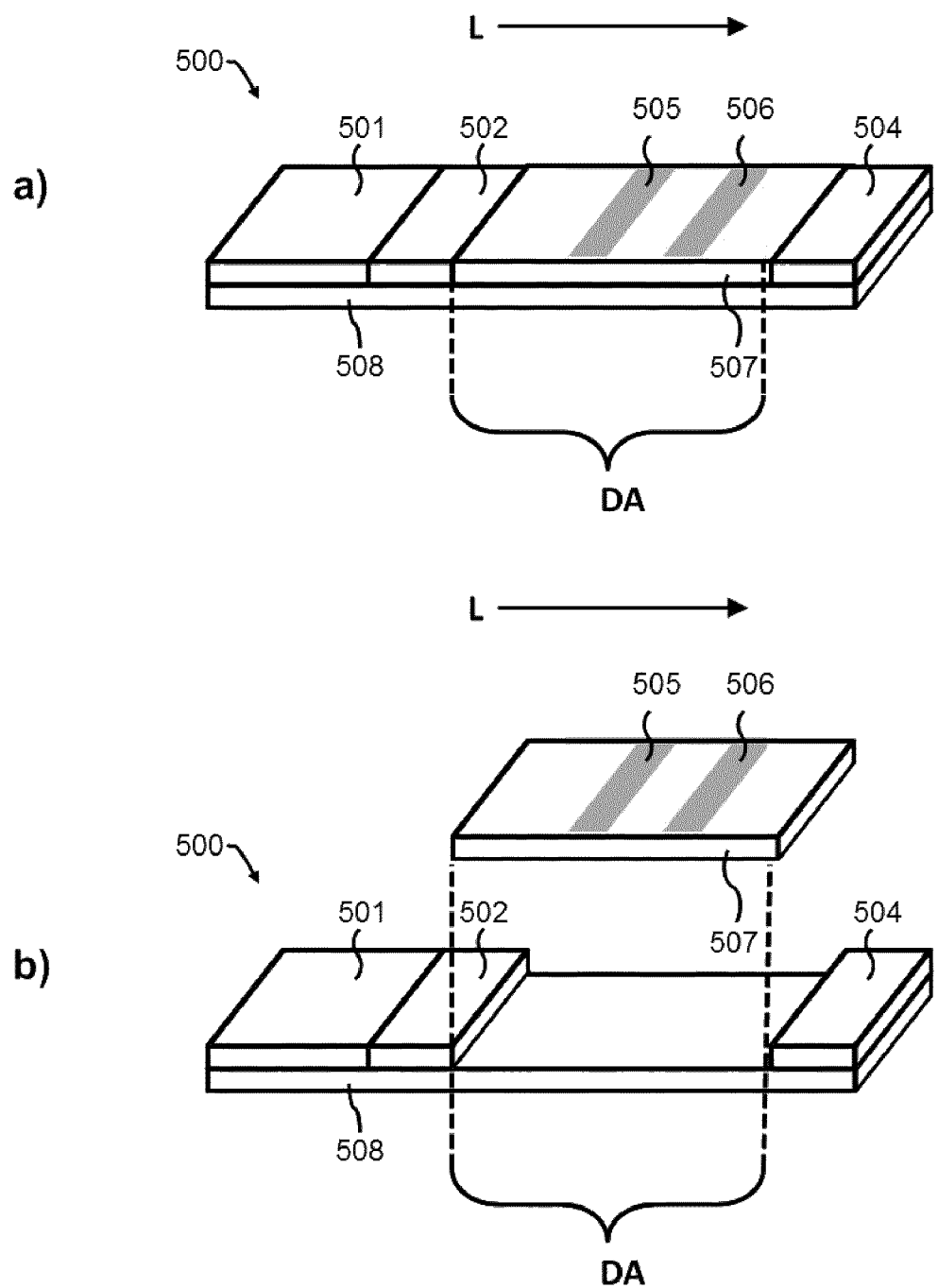
FIG. 5 shows perspective views of different embodiments, of the present invention, of a lateral flow assay strip (500).

Detecting IL-8 and hBD-1 with the Device According to FIG. 4

This is an example showing that a separate insert of a detection area (411, 507) separate from the lateral flow assay device (400) can be used in the lateral flow assay to detect IL-8 and hBD-1 from the human skin.

Materials

| | |
|---|---|
| Capture antibodies: | 100 ug/ml in 1xPBS: Rabbit anti-Human BD-1, and Goat anti-Human CXCL8/IL-8 |
| Detector antibodies: | Conjugated to 40 nm Colloidal Gold at 10 ug/mL: Rabbit anti-Human BD-1, and Mouse anti-Human CXCL8/IL-8 |
| Antigens: | Various levels 0-50 ng/ml in Running buffer Recombinant Human BD-1, and Recombinant Human CXCL8/IL-8 |
| Running buffer: | 25 mM Tris, 1% Pentasodium Tripolyphosphate, 0.1% Sodium Azide, 0.1% TritonX-405, 2 mM EDTA, 0.5% Sodium Casein, pH 8.0 |
| Analysis membrane (411, 507): | Sartorius CN140, with capture antibodies, blocked with blocking buffer: 10 mM Sodium Phosphate, 0.1% Sucrose, 0.1% BSA, 0.2% PVP-40, pH 7.2 |
| Wicking pad (404, 504): | Millipore CO95 |
| Conjugate pad (502): | Millipore G041, Blocking buffer: 10 mM Borate, 3% BSA, 1% PVP-40, 0.25% Tritonx-100, pH 8.0 |
| Sample pad (elution zone) (401, 501): | Millipore G041 |

Calibration of Test Sensitivity

Figure 7:
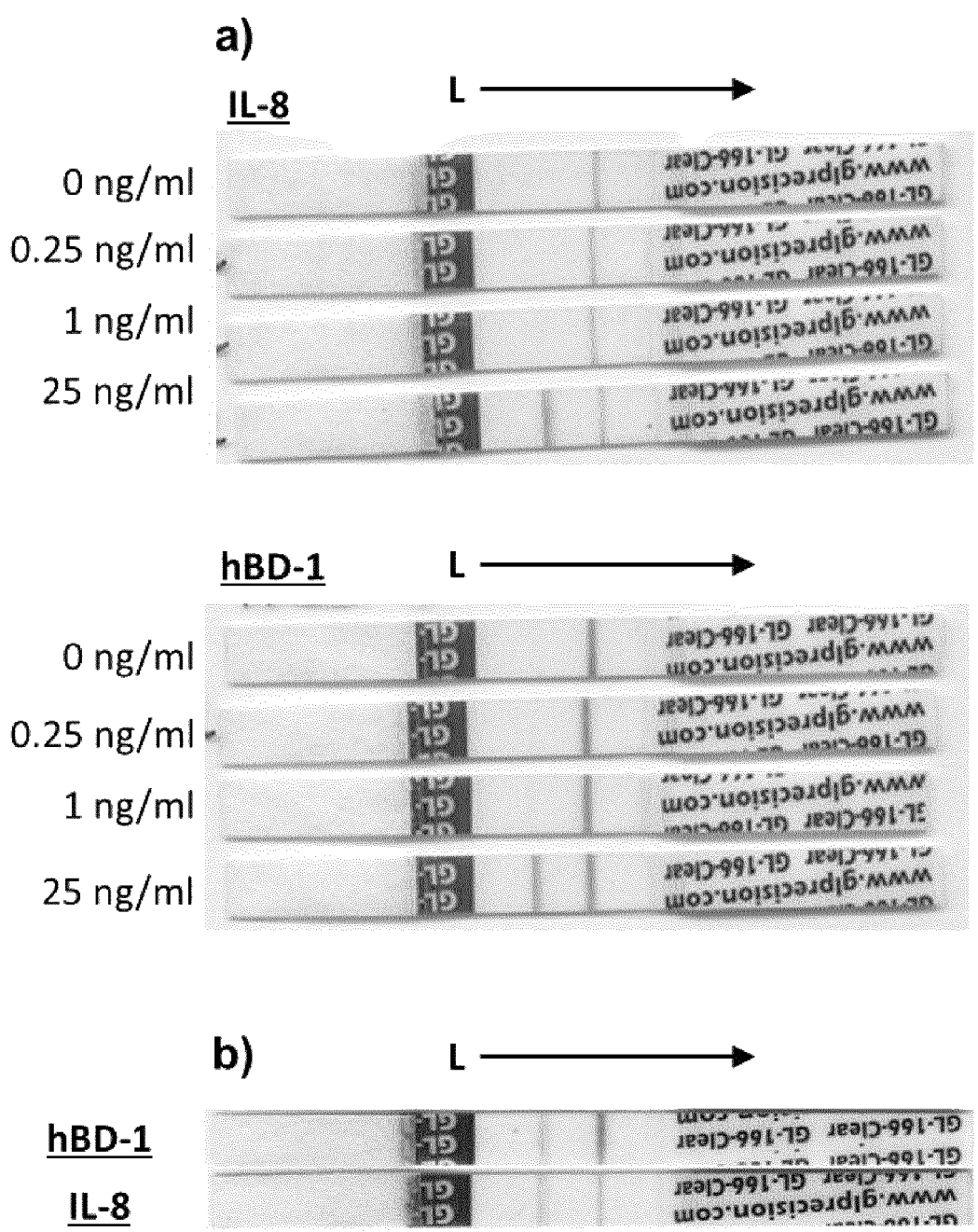
FIG. 7 shows the sensitivity of a lateral flow assay device according to example 2, where in FIG. 7a different concentrations of analytes added directly to the detection area (DA) were analysed. Controls (right) and analytes (left) shows this a level of visual detection of IL-8 detection to be around 1 ng/ml and that the level of visual detection of hBD-1 to be around 0.25 ng/ml.

Analytes IL-8 and hBD1 were diluted in running buffer to concentrations 0.25, 1 and 25 ng/ml and used for determining sensitivity for this particular setup (FIG. 7a). For testing, analytes were added to the detection area membrane (50 µl) following assembly of the analysis cassette and adding 100 µl of running buffer.

The lateral flow strips of FIG. 7a shows the level of visual detection of IL-8 to be around 1 ng/ml and that the level of visual detection of hBD-1 to be around 0.25 ng/ml.

To analyze IL-8 and hBD-1 from the skin, a detection area (411, 507) was wetted with 25 µl of milliQ water and placed in contact with a lesional area of contact dermatitis skin for 15 minutes, inserted into the lateral flow assay cassette (410) and developed by adding 100 µl of running buffer.

The lateral flow strip is shown in FIG. 7b where it can be seen that IL-8 and hBD-1 (left) can be detected from a sample obtained from the skin surface. Controls are shown (right).

Example 3

Example Showing the Effect of the Expanding Layer (212)

The effect of an expandable layer in the sampling step is tested. It can be seen that stable and reliable results of skin analysis are obtained using a sample pad configuration of the lateral flow device (FIGS. 1, 2 and 3) to detect IL-8 and hBD-1 from the human skin.

Materials

| | |
|---|---|
| Capture antibodies: | 100 ug/ml in 1xPBS: Rabbit anti-Human BD-1, and Goat anti-Human CXCL8/IL-8 |
| Detector antibodies: | Conjugated to 40 nm Colloidal Gold at 10 ug/mL: Rabbit anti-Human BD-1, and Mouse anti-Human CXCL8/IL-8 |
| Antigens: | Various levels 0-50 ng/ml in Running buffer Recombinant Human BD-1, and Recombinant Human CXCL8/IL-8 |
| Running buffer: | 25 mM Tris, 1% Pentasodium Tripolyphosphate, 0.1% Sodium Azide, 0.1% TritonX-405, 2 mM EDTA, 0.5% Sodium Casein, pH 8.0 |

| | |
|---|---|
| Analysis membrane (307): | Sartorius CN140, with capture antibodies, blocked with blocking buffer: 10 mM Sodium Phosphate, 0.1% Sucrose, 0.1% BSA, 0.2% PVP-40, pH 7.2 |
| Wicking pad (304, 104): | Millipore CO95 |
| Conjugate pad (302, 102): | Millipore G041, Blocking buffer: 10 mM Borate, 3% BSA, 1% PVP-40, 0.25% Tritonx-100, pH 8.0 |
| Sample pad (collection pad) (201): | Millipore G041 |
| Lateral flow strip reader: | ESE Reader, ID: ESLF34-MB-4501, SN: P0082 (Qiagen) |
| Expandable layer/membrane (212): | ¼" compressed cellulose sponge, Industrial Commercial Supply |

Comparison of analysis results obtained using the sample pad with and without expandable layer shows that expandable layer improves the reproducibility and quality of analysis results, as evident from the below table 1.

The table shows the effect of the expandable layer on the detection level and variation of the skin analysis results. Sample pads with and without expandable material (in the sample pads without expandable material, the expandable material was exchanged with a non-expandable material) having two different capture antibodies, IL-8, hBD-1 were each wetted with mQ water (150 µl) after being releasably fastened to 4 individuals, each individual was analysed with 3 patches. The sample pads were exposed for 15 minutes on the skin area of contact dermatitis following identical processing. Level of analytes was quantified using standard curves and lateral flow strip reader. Average concentration, standard deviation and standard deviation % were calculated.

| Sample pad with expandable material | | Standard deviation in % |
|---|---|---|
| | Average of IL-8 concentration (ng/ml) from 3 sample pads | |
| Person no. 1 | 3.5 ± 0.2 | 5.7% |
| Person no. 2 | 8.6 ± 0.5 | 5.8% |
| Person no. 3 | 13.0 ± 0.8 | 6.1% |
| Person no. 4 | 7.7 ± 0.5 | 6.4% |
| | Average of hBD-1 concentration (ng/ml) from 3 sample pads | |
| Person no. 1 | 12.5 ± 0.3 | 2.4% |
| Person no. 2 | 15.0 ± 0.5 | 3.3% |
| Person no. 3 | 9.8 ± 0.4 | 4.1% |
| Person no. 4 | 17.5 ± 0.6 | 3.4% |

| Sample pad without expandable material | | Standard deviation in % |
|---|---|---|
| | Average of IL-8 concentration (ng/ml) from 3 sample pads | |
| Person no. 1 | 2.4 ± 0.9 | 37.5% |
| Person no. 2 | 3.6 ± 1.4 | 38.9% |
| Person no. 3 | 9.6 ± 5.1 | 53.1% |
| Person no. 4 | 3.1 ± 1.8 | 58.1% |
| | Average of hBD-1 concentration (ng/ml) from 3 sample pads | |
| Person no. 1 | 6.9 ± 0.9 | 13.0% |
| Person no. 2 | 3.7 ± 1.9 | 51.4% |
| Person no. 3 | 4.1 ± 1.6 | 39.0% |
| Person no. 4 | 11.3 ± 5.8 | 51.3% |

It can be seen from the readings that devices with an expandable layer in sample pad resulted in significantly higher value of analytes, and resulted in significantly lower standard deviation and standard deviation % compared to the sample pads without expandable material.

This higher sensitivity and lower variation of analysis from the devices with the expandable layer is related to firm and homogenous contact of the sample pad material with the skin due to constant pressure created by the expandable layer.

The invention claimed is:

1. A diagnostic kit for detecting the presence or quantity of one or more test analytes within a test sample taken from a skin surface of a mammal, the diagnostic kit comprising:
    a) a separate insert for a lateral flow device comprising a membrane fixed to a rigid support frame, the membrane having a thickness, a width, a length, and a bottom for contacting the skin surface, to obtain the test sample,
    b) a lateral flow assay device comprising a housing and an opening for accepting the separate insert to an interior of the housing, wherein the lateral flow assay device comprises an elution zone and a detection area, and wherein the separate insert is the elution zone, and not the detection area,
    c) a securing member comprising at least one adhesive surface portion on a bottom side of the securing member for releasably attaching the separate insert to the skin surface of the mammal, wherein the securing member comprises an expandable layer extending from the at least one adhesive surface portion on the bottom side of the securing member to apply pressure to a top side of the rigid support frame of the separate insert and thereby pressing the separate insert against the skin surface of the mammal, wherein the expandable layer is not in fluid communication with the separate insert.

2. The diagnostic kit of claim 1, wherein the lateral flow device is constructed so as to form a capillary bed, when it is mated with the separate insert, wherein the lateral flow device mated with the separate insert comprise an elution zone and a detection area, as well as one or more of the following: a conjugate pad and a wicking pad.

3. The diagnostic kit of claim 2, wherein the detection area comprise a detection zone containing one or more affinity molecule(s) for selectively retaining one or more test analyte(s) and optionally an indicator zone containing one or more affinity molecule(s) for selectively retaining one or more indicator affinity molecule(s).

4. The diagnostic kit of claim 1, wherein the membrane has a thickness equal to 4 mm or less, and a width and a length, both greater than the thickness, wherein the lateral flow device is configured to have a lateral flow direction (L) substantially in the direction of a plane created by the width and the length of the membrane.

5. The diagnostic kit of claim 1, wherein the rigid support frame covers the perimeter of the membrane.

6. The diagnostic kit of claim 1, wherein the expandable layer of the securing member contains compressed cellulose.

7. The diagnostic kit of claim 1, wherein the one or more test analyte(s) are selected from the group consisting of:

chemokines, interleukins, growth factors, hormones, enzymes, and other molecules present on the skin of a mammal.

8. The diagnostic kit of claim 1, wherein the one or more test analyte(s) are selected from the group consisting of: Interleukin 1 alpha (IL-1a), Interleukin 1 beta (IL-1b), interleukin-1 receptor antagonist (IL-1RA), Interleukin 8 (IL-8), C-C Motif Chemokine Ligand 2 (CCL-2), C-C Motif Chemokine Ligand 5 (CCL-5), C-C Motif Chemokine Ligand 27 (CCL-27), C-X-C motif chemokine ligand 1 (CXCL-1), C-X-C motif chemokine ligand 2 (CXCL-2), C-X-C motif chemokine ligand 9 (CXCL-9), Trappin2/Elafin, human Beta-defensin 1 (hBD-1), human Beta-defensin 2 (hBD-2), Vascular endothelial growth factor (VEGF), and Thymic stromal lymphopoietin (TSLP).

9. The diagnostic kit of claim 1, wherein there is an inert backing layer between the expandable layer and the membrane.

* * * * *